United States Patent
Saiwaki et al.

(10) Patent No.: US 8,969,088 B2
(45) Date of Patent: Mar. 3, 2015

(54) SUBSTRATE MIMICKING INTERCELLULAR LIPIDS IN STRATUM CORNEUM AND METHOD OF EVALUATING SKIN ROUGHENING USING THE SAME

(75) Inventors: Takuya Saiwaki, Yokohama (JP); Takashi Oka, Yokohama (JP); Yuichiro Mori, Yokohama (JP); Toyoko Imae, Yokohama (JP); Xiaojuan Wang, Yokohama (JP); Masaki Ujihara, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 33 days.

(21) Appl. No.: 12/998,985

(22) PCT Filed: Sep. 1, 2009
(Under 37 CFR 1.47)

(86) PCT No.: PCT/JP2009/065268
§ 371 (c)(1),
(2), (4) Date: Oct. 7, 2011

(87) PCT Pub. No.: WO2010/073777
PCT Pub. Date: Jul. 1, 2010

(65) Prior Publication Data
US 2013/0000394 A1 Jan. 3, 2013

(30) Foreign Application Priority Data
Dec. 26, 2008 (JP) ................. 2008-335319

(51) Int. Cl.
*G01B 21/30* (2006.01)
*G01N 33/92* (2006.01)
*C09K 3/00* (2006.01)

(52) U.S. Cl.
CPC ............ *G01N 33/92* (2013.01); *G01N 2800/20* (2013.01)
USPC ......... 436/71; 252/408.1; 73/105; 73/204.26; 73/104; 424/283.1; 436/13; 436/60; 514/7.4

(58) Field of Classification Search
USPC .................... 73/105, 104, 204.26; 252/408.1; 514/53, 78, 7.4; 536/53; 554/78; 436/71, 13, 60; 424/283.1
See application file for complete search history.

(56) References Cited

U.S. PATENT DOCUMENTS

2006/0258616 A1* 11/2006 Wolf et al. .......................... 514/53
2008/0286364 A1* 11/2008 Ogiwara et al. ............... 424/489
2009/0233319 A1 9/2009 Katagiri et al.

FOREIGN PATENT DOCUMENTS

CN 2132488 Y 5/1993
CN 1850021 A 10/2006
(Continued)

OTHER PUBLICATIONS

International Search Report mailed Dec. 8, 2009, in PCT/JP2009/065268, 2 pages.
(Continued)

*Primary Examiner* — Rebecca M Fritchman
(74) *Attorney, Agent, or Firm* — Foley & Lardner LLP

(57) ABSTRACT

A substrate mimicking intercellular lipids in stratum corneum consisting of a substrate and a lipid membrane formed on the substrate, wherein the lipid membrane is formed from ceramide, palmitic acid and cholesterol, and the ceramide, palmitic acid and cholesterol are present at a mass ratio of 20-70%: 10-60%:20-40% (ceramide:palmitic acid:cholesterol).

5 Claims, 10 Drawing Sheets

(56) References Cited

FOREIGN PATENT DOCUMENTS

| | | |
|---|---|---|
| CN | 101142483 A | 3/2008 |
| WO | WO 2008/143145 A1 | 11/2008 |

OTHER PUBLICATIONS

Kai et al,. "A method for assessing percutaneous permeability by using model lipids of stratum corneum," Xenobiotic Metabolism and Disposition, 1994, 9(Supp):S82-S85, English abstract on last page.

Kai et al., "Keratinized Epithelial Transport of Beta-Blocking Agents. II. Evaluation of Barrier Property of Stratum Corneum by Using Model Lipid Systems," Biol. Pharm. Bull., 1993, 16(3):284-287.

Lafleur, Michel, "Phase behaviour of model stratum corneum lipid mixtures: an infrared spectroscopy investigation," Can. J. Chem., 1998, 76(11):1501-1511.

McIntosh, Thomas J., "Organization of Skin Stratum Corneum Extracellular Lamellae: Diffraction Evidence for Asymmetric Distribution of Cholesterol," Biophysical Journal, Sep. 2003, 85:1675-1681.

Moore et al., "Kinetics of Membrane Raft Formation: Fatty Acid Domains in Stratum Corneum Lipid Models," J. Phys. Chem. B, 2006, 110(5):2378-2386.

Matsuzaki et al., "Development of a Model Membrane System Using Stratum Corneum Lipids for Estimation of Drug Skin Permeability," Chem. Pharm. Bull., Mar. 1, 1993, 41(3):575-579.

Pilgram et al., "Study on the lipid organization of stratum corneum lipid models by (cryo-) electron diffraction," Journal of Lipid Research, Aug. 1, 1998, 39(1):1669-1676.

Rowat et al., "Interactions of oleic acid and model stratum corneum membranes as seen by $^2H$ NMR," International Journal of Pharmaceutics, Jan. 31, 2006, 307(2):225-231.

Uhoda et al., "Repair Kinetics of the Stratum corneum under Repeated Insults," Exogenous Dermatology, 2004, 3(1):7-11.

\* cited by examiner

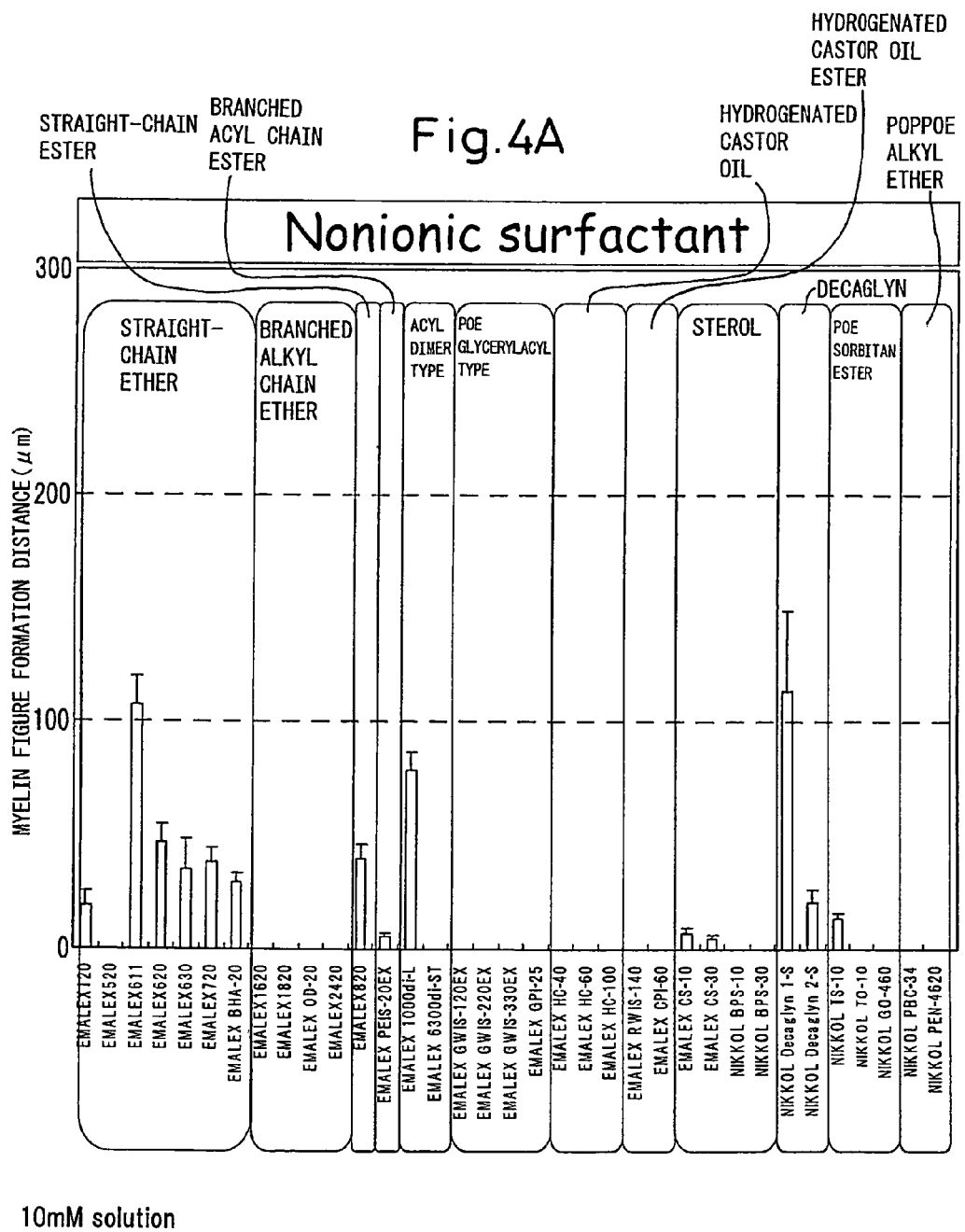

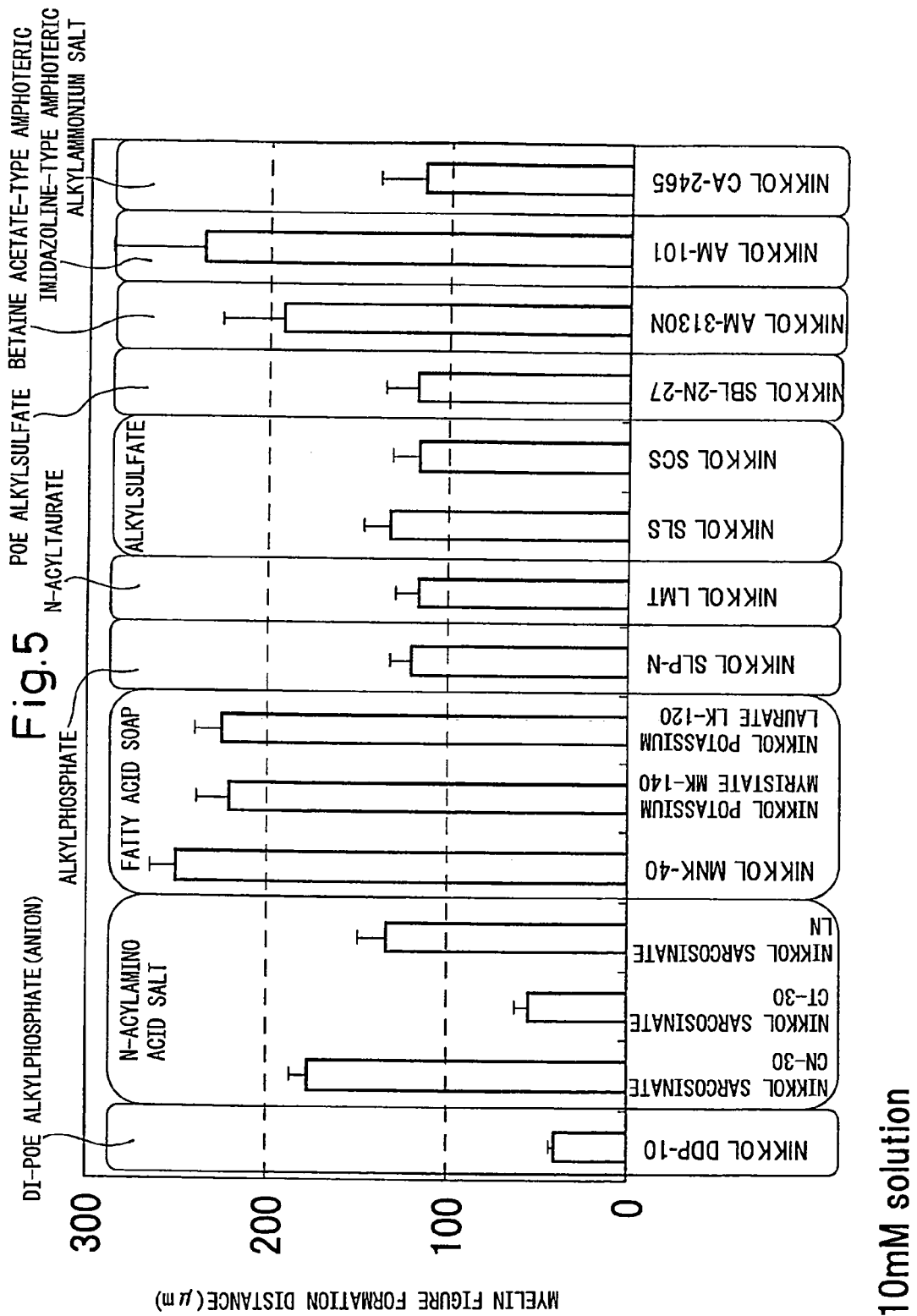

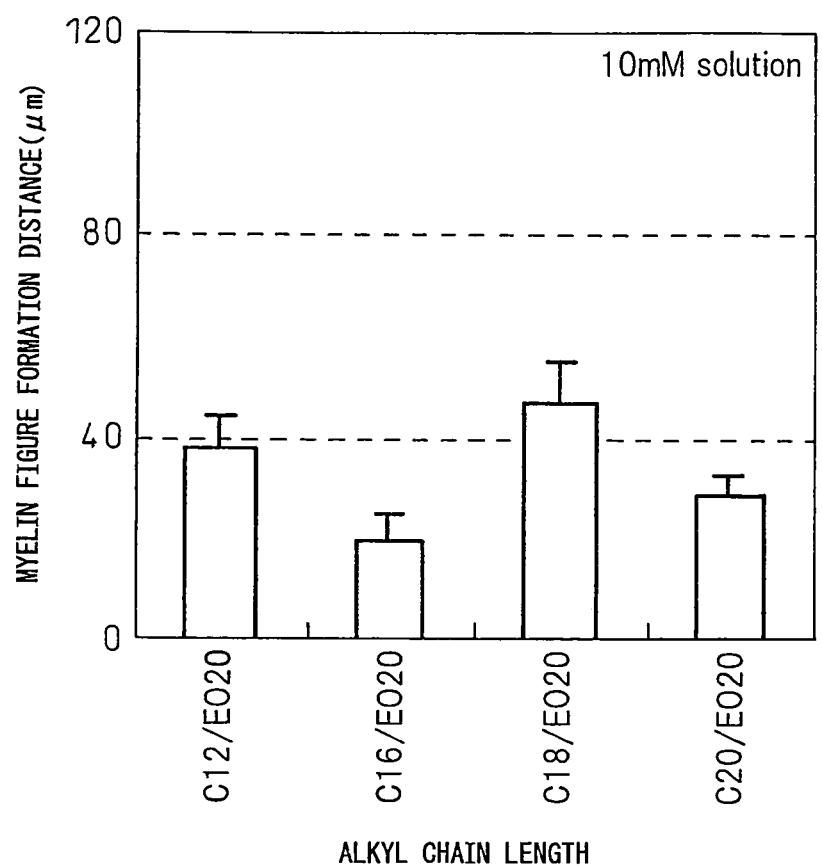

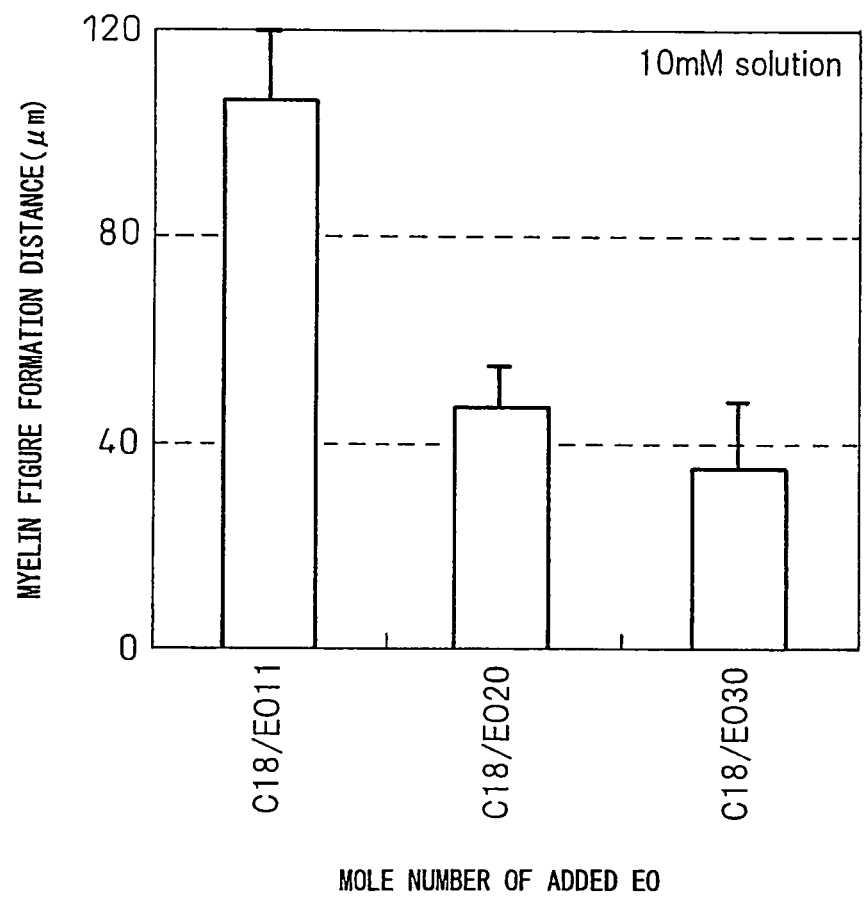

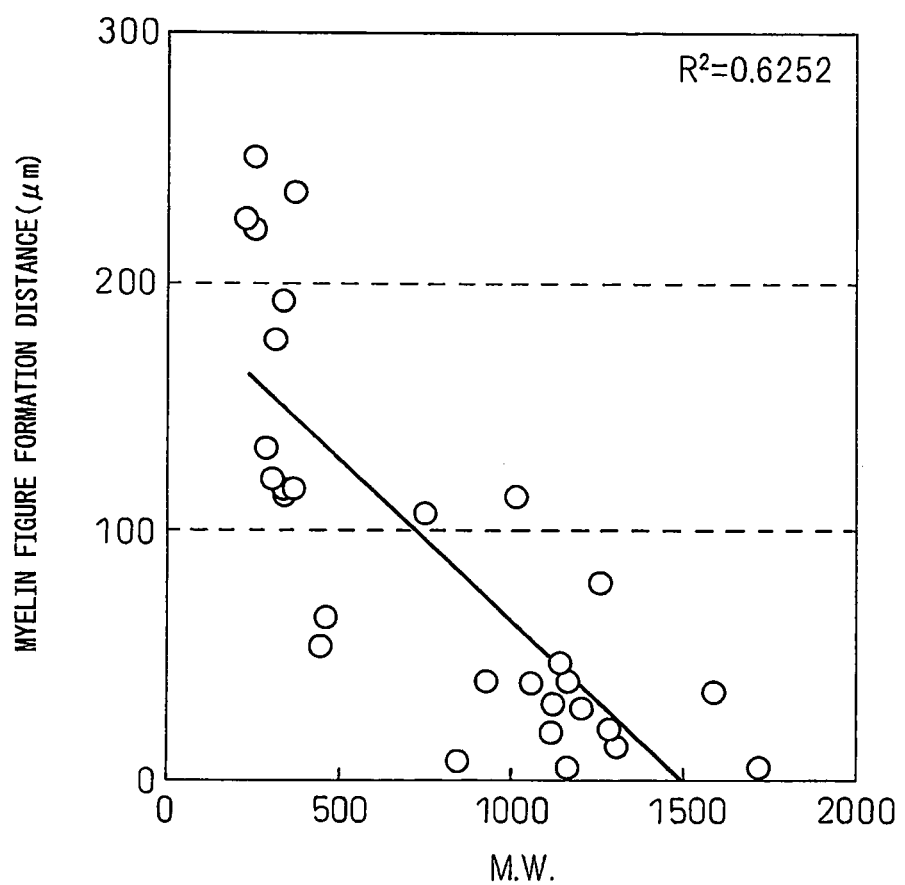

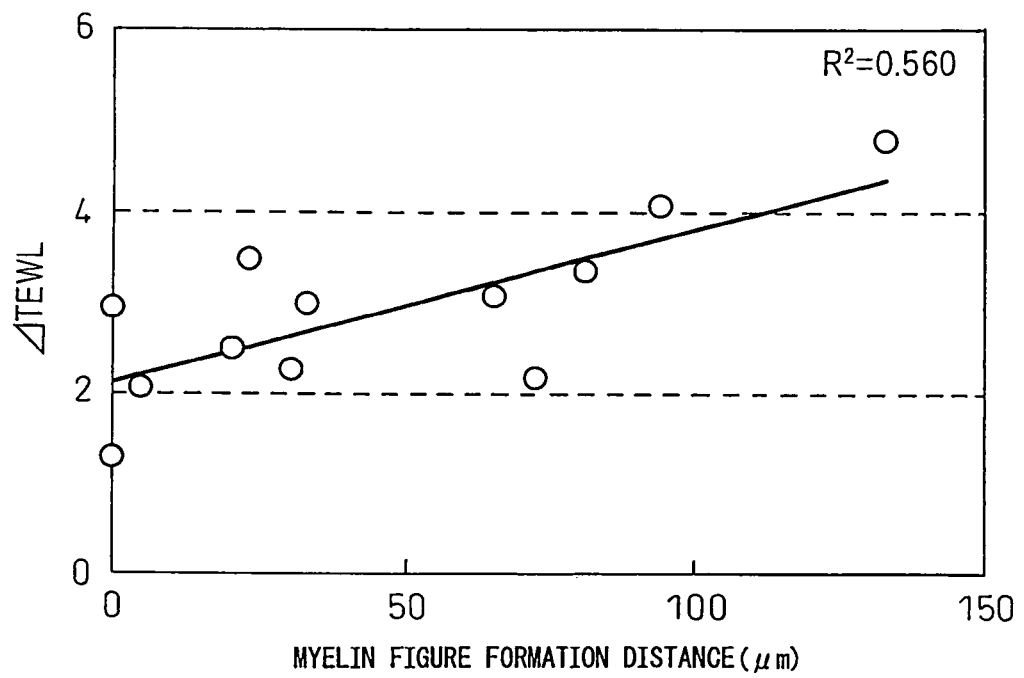

SUBSTRATE MIMICKING INTERCELLULAR LIPIDS IN STRATUM CORNEUM AND METHOD OF EVALUATING SKIN ROUGHENING USING THE SAME

CROSS-REFERENCE TO RELATED APPLICATIONS

This application is a National Stage application of PCT/JP2009/065268, filed Sep. 1, 2009, which claims priority from Japanese application JP 2008-335319, filed Dec. 26, 2008.

TECHNICAL FIELD

The present invention relates to a novel in vitro model substrate which mimics stratum corneum intercellular lipids, and to a method of evaluating skin roughening using the substrate.

BACKGROUND ART

The stratum corneum, located on the outermost layer of skin, has a barrier function that protects the body from contact and infiltration of foreign matter such as bacteria and hazardous substances, while also maintaining skin in a healthy state by preventing transpiration of moisture from the body. When the barrier function is impaired, transepidermal water loss (TEWL) from the skin surface increases, thus lowering the relative moisture content in stratum corneum. Reduction of moisture content in stratum corneum, resulting in an irregular texture of dermatoglyphs composed of sulci cutis and cristae cutis, creates a dry, roughened skin condition (Sone, T. et al., Koshokaishi, Vol. 15 No. 2. pp. 60-65 (1991)).

The intercellular lipids in the stratum corneum, which play an important role in the barrier function, are composed mainly of ceramides, free fatty acids and cholesterol, and they are known to form a lamellar structure (Bouwstra J A, et al., Acta Derm Venereol Suppl (Stockh). 2000 208: pp. 23-30; Bouwstra J A, et al., Int J Cosmet Sci. 2008 Oct. 30(5): p. 388). For development of cosmetics, it is necessary to examine the interaction between stratum corneum intercellular lipids and cosmetic materials beforehand to avoid impairing the barrier function of the skin, and to screen for effective materials.

For examination of the effects of cosmetic materials on skin barrier function, usually a biological sample is exposed to the candidate material and then its intercellular lipid structure is subjected to X-ray analysis, electron spin resonance (ESR), differential scanning calorimetry (DSC), infrared ray analysis (IR) or the like. Using a biological sample allows the necessary data to be obtained which can be linked directly to product information.

However, because of individual differences in biological samples, the stratum corneum intercellular lipids obtained from the samples also have different structures that depend on the particular sample. Furthermore, complex procedures are required to obtain specific stratum corneum intercellular lipids from animals, and measuring methods are limited in light of animal protection.

For development of new cosmetics, therefore, it has been necessary to employ convenient and highly reproducible indicators that do not rely on biological samples, in order to determine what effects the substances have on stratum corneum intercellular lipids.

Surfactants are among the components included in skin care products and the like. Surfactants penetrate the stratum corneum and are absorbed into the keratin of cornified cells, mixing with intercellular lipids (Friberg, S. E. et al., Colloids Surf. 1988, 30, pp. 1-12; Rhein, L. D. Ibid. 1997, 48, pp. 253-274). Surfactants are also known to remove cutaneous lipids such as fatty acids, fatty acid glycerides and cholesteryl esters, thus incurring damage to the skin even if the removed lipids are minimal (Fulmer, A. W. et al., J. Invest. Dermatol. 1986, 86, pp. 598-602; Denda, M. et al., Arch. Dermatol. Res. 1994, 286, pp. 41-46; Ronald, R. W. et al., J. Invest. Dermatol. 1999, 113, pp. 960-966; Lopez, O. et al. Bioch. et Biophy Acta 2000, 1508, pp. 196-209; Ebba, B. et al., Inter J. Pharma. 2000, 195, pp. 189-195).

The effects of surfactants on stratum corneum intercellular lipids have been an object of interest in the past in connection with the skin barrier function (Harada, K. et al, J. Invest. Dermatol. 1992, 99, pp. 278-282; Lavrijsen, A. P. M. et al., J. Invest. Dermatol. 1995, 105, pp. 619-624), and as regards changes in lipid composition related to various cutaneous symptoms (Holleran, W. M. et al, J. Lipid Res. 1991, 32, pp. 1151-1158; Murata, Y. et al., J. Invest. Dermatol. 1996, 106, pp. 1242-1249; Ponec, M. et al, J. Invest. Dermatol. 1997, 109, pp. 348-355). Nevertheless, the action processes and mechanisms are still poorly understood.

CITATION LIST

Non-Patent Literature

[Non-patent document 1] Sone, T. et al., Koshokaishi, Vol. 15 No. 2. pp. 60-65 (1991).

[Non-patent document 2] Bouwstra J A, et al., Acta Dem Venereol Suppl (Stockh). 2000; 208: pp. 23-30

[Non-patent document 3] Bouwstra J A, et al., Int J Cosmet Sci. 2008 October; 30(5): p. 388

[Non-patent document 4] Friberg, S. E. et al., Colloids Surf. 1988, 30, pp. 1-12

[Non-patent document 5] Rhein, L. D. Ibid. 1997, 48, pp. 253-274

[Non-patent document 6] Fulmer, A. W. et al., J. Invest. Dermatol. 1986, 86, pp. 598-602

[Non-patent document 7] Denda, M. et al., Arch. Dermatol. Res. 1994, 286, pp. 41-46

[Non-patent document 8] Ronald, R. W. et al., J. Invest. Dermatol. 1999, 113, pp. 960-966

[Non-patent document 9] Lopez, O. et al. Bioch. et Biophy Acta 2000, 1508, pp. 196-209

[Non-patent document 10] Ebba, B. et al., Inter J. Phama. 2000, 195, pp. 189-195

[Non-patent document 11] Harada, K et al, J. Invest. Dermatol. 1992, 99, pp. 278-282

[Non-patent document 12] Lavrijsen, A. P. M. et al, J. Invest. Dermatol. 1995, 105, pp. 619-624

[Non-patent document 13] Holleran, W. M. et al, J. Lipid Res. 1991, 32, pp. 1151-1158

[Non-patent document 14] Murata, Y. et al., J. Invest. Dermatol. 1996, 106, pp. 1242-1249

[Non-patent document 15] Ponec, M. et al, J. Invest. Dermatol. 1997, 109, pp. 348-355

[Non-patent document 16] O. Lopez et al., J. dispersion science and technology, 18 (5), pp. 503-515 (1997)

DISCLOSURE OF THE INVENTION

Problems to be Solved by the Invention

It is an object of the present invention to provide an in vitro substrate modeled on stratum corneum intercellular lipids, which has high structural homogeneity and allows easy measurement of structural changes in lipids, and a method of evaluating skin roughening using the substrate.

Means for Solving the Problems

As a simple skin model for the stratum corneum, the present inventors formed a lipid mixture composed of the three components ceramide, palmitic acid and cholesterol on a substrate such as cover glass, and found that the lipid membrane formed on the substrate is similar to the lipid lamellar structure of the stratum corneum, and as a result of analyzing the physical properties thereof, it was found that the nature of the lipid membrane is similar to the intercellular lipids of the stratum corneum. Considering the lamellar structure and the results of analyzing the physical properties, the lipid membrane formed by the mixed lipids composed of the three components is concluded to be similar to the intercellular lipid structure of the stratum corneum.

It is known that when a surfactant is applied to porcine skin, the stratum corneum lipid structure is converted from a lamellar structure to a vesicular form (O. Lopez et al., J. Dispersion Science and Technology, 18(5), pp. 503-515 (1997)). The present inventors therefore added specific surfactants to a lipid membrane formed from the aforementioned lipid mixture, and found that the stratum corneum lipid structure was disrupted and the molecules composing the lipid membrane assembled into tubes, creating a myelin figure. Upon examining the relationship between the distance from the tip of the myelin figure to the edge of the lipids-mimicking substrate, and the TEWL value as evaluation of the skin barrier function, a correlation was found between the two.

Based on this knowledge, the present inventors reached the conclusion that the lipid membrane composed of the three components of ceramide, palmitic acid and cholesterol can serve as an in vitro model for stratum corneum intercellular lipids, and that quantitative and qualitative evaluation of the myelin figure formed by adding specific surfactants to the lipid membrane can serve as an index for measurement of the interaction between the stratum corneum intercellular lipids and cosmetic materials.

Specifically, the scope of the invention encompasses the following.

[1] A stratum corneum intercellular lipids-mimicking substrate, consisting of a substrate and a lipid membrane formed on the substrate, wherein the lipid membrane is formed of ceramide, palmitic acid and cholesterol.

[2] A stratum corneum intercellular lipids-mimicking substrate according to [1], wherein the ceramide, palmitic acid and cholesterol are present in a mass ratio of 20-70%:10-60%:20-40% (ceramide:palmitic acid:cholesterol).

[3] A method for evaluating skin roughening, wherein a surfactant is added to a stratum corneum intercellular lipids-mimicking substrate according to [1] or [2], and the surfactant is evaluated as causing skin roughening in vivo if a myelin figure is formed on the substrate, and the degree of skin roughening is evaluated as poorer the longer the shortest distance between the tip of the myelin figure and the edge of the substrate.

Effect of the Invention

The substrate that mimics stratum corneum intercellular lipids according to the invention (hereunder referred to throughout the present specification as "substrate mimicking intercellular lipids in stratum corneum" or "lipids-mimicking substrate") is a simplified model membrane composed of 3 different lipids (ceramide, palmitic acid and cholesterol), as the major constitutive substances of the stratum corneum which has a complex structure. A myelin figure is formed by addition of specific surfactants to the substrate of the invention. Depending on the type of surfactant added, the distance from the tip of the myelin figure to the edge of the substrate is long in some cases. Surfactants that increase this distance also increase the TEWL value in human patch tests. Since an increase in TEWL value corresponds to a reduced skin barrier function, the lipids-mimicking substrate of the invention may be used for in vitro evaluation of the interaction between stratum corneum intercellular lipids and cosmetic materials, and thus of the effects of cosmetic materials on skin roughening, without using a biological sample.

Upon evaluating surfactants that form a myelin figure, by a patch test or a test using collagen or interleukin-8, no correlation was found between myelin figure formation and cellular toxicity. Thus, it is believed that the lipids-mimicking substrate of the invention can be applied to skin roughening test methods that are specialized for evaluating reduction in skin barrier function (disruption of the stratum corneum lipid structure).

BRIEF DESCRIPTION OF THE DRAWINGS

FIG. 4A is a graph showing the relationship between the nonionic surfactants and the distances at which the myelin figures were formed.

FIG. 5 is a graph showing the relationship between the ionic surfactant and the distances at which the myelin figure were formed.

FIG. 7 is a graph showing the relationship between the alkyl chain lengths of the surfactant and the distances at which the myelin figures were formed.

FIG. 8 is a graph showing the relationship between the mole number of added EO of the surfactants and the distances at which the myelin figures were formed.

FIG. 9 is a graph showing the relationship between the molecular weight of the surfactants and the distances at which the myelin figures were formed.

FIG. 10 is a graph showing the relationship between the distance at which the myelin figure is formed, and the ΔTEWL value.

BEST MODE FOR CARRYING OUT THE INVENTION

Substrate Mimicking Intercellular Lipids in Stratum Corneum

According to a first aspect of the invention, there is provided a substrate mimicking intercellular lipids in stratum corneum consisting of a substrate and a lipid membrane formed on the substrate, wherein the lipid membrane is formed from ceramide, palmitic acid and cholesterol, and the ceramide, palmitic acid and cholesterol are present at a mass ratio of 20-70%:10-60%:20-40% (ceramide:palmitic acid: cholesterol).

For the lipids-mimicking substrate of the invention, a plate such as cover glass, mica or a silicon wafer is used as the basic substrate for formation of the lipid membrane. If the material of the substrate is desired to be treated to obtain a smooth surface and to have heat resistance, a metal such as stainless steel or a ceramic can be used for the substrate. The lipid membrane employs a lipid mixture, for example, a lipid mixture comprising ceramide, palmitic acid and cholesterol, as a constituent material. Of the ceramide in the lipid mixture, ceramide III is preferred as it has the most standard structure and is inexpensive.

The lipid mixture is dissolved in a solvent at 20-700:10-60%:20-400 (ceramide:palmitic acid:cholesterol) as the mass, ratio. From the viewpoint of mimicking the compositional ratio of stratum corneum intercellular lipids present in the skin, the proportion of the mixed lipids is preferably a mass ratio of 2:1:1 (ceramide:palmitic acid:cholesterol). The solvent used may be methanol, chloroform, hexane, acetone, ethyl acetate or the like, or a mixture thereof. The solvent is not limited to these specific solvents, and may be any one that is capable of dissolving the lipids.

After the lipid mixture has been dissolved in the solvent, the solution is developed on a plate, such as cover glass, and dried. Next, the plate is melted in an oven at high temperature (for example, 120° C.) and allowed to stand for a prescribed period of time under a nitrogen stream. After cooling to room temperature, the plate may be wetted by addition of water or immersed (for example, extended dipping in water or water addition), to prepare a lipids-mimicking substrate of the invention. A method of wetting the solid lipid mixture after melting may also be employed.

Skin Roughening Evaluation Method Using Lipids-Mimicking Substrate

According to a second aspect of the invention there is provided a method of evaluating skin roughening, which comprises measuring the distance between the tip of the myelin figure formed by addition of a surfactant to a substrate mimicking intercellular lipids in stratum corneum, and the edge of the substrate, and using the increase in distance as an indicator of skin roughening.

Figure 1:
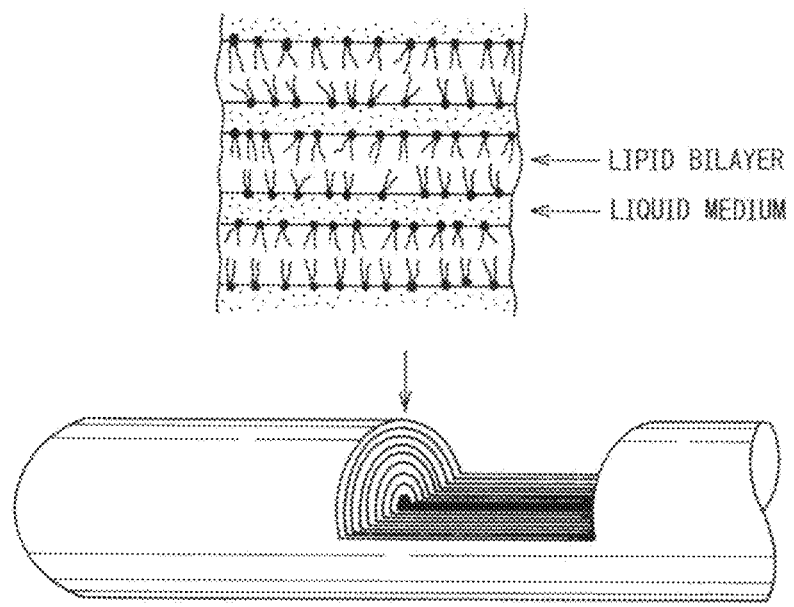
FIG. 1 is a schematic view of a myelin figure.

A myelin figure is an aggregate of tube-shaped molecules formed when the molecules are in a liquid crystal state in water (FIG. 1). A myelin figure is generally formed when a lyotropic smectic A phase (a type of liquid crystal) contacts with an appropriate medium. Formation of the myelin figure can be visually confirmed with a microscope after a specific surfactant has been added to the substrate.

Multiple myelin figures are formed in a specific range from the substrate of the invention by addition of specific surfactants. The range differs depending on the type of surfactant added. A longer distance from the edge of the substrate to the tip of the formed myelin figure corresponds to increased transepidermal water loss (TEWL) from skin to which the same surfactant has been applied. In other words, when the distance between the myelin figure formed by addition of a given surfactant and the substrate is long, application of that surfactant to human skin is expected to disrupt the stratum corneum lipid structure and cause skin roughening.

"Skin roughening" refers to a condition of increased TEWL (transdermal moisture transpiration) compared to the one prior to application of a test substance, for example, and a larger increase in TEWL corresponds to a lower skin barrier function. In the evaluation method of the invention, however, "skin roughening" is considered to be a condition in which a myelin figure is formed upon application of a test substance to the substrate mimicking intercellular lipids in stratum corneum. Since the range in which the myelin figure is formed on the substrate of the invention is correlated with the TEWL value, a larger range can be evaluated as a poorer degree of skin roughening when the test substance is actually applied to skin. For reproducibility by this evaluation method, the shortest distance between the tip of the myelin figure and the interface of the substrate is used as an indicator of aggravated skin roughening according to the invention.

When the shortest distance between the tip of the myelin figure and the edge of the stratum corneum intercellular lipid substrate is used as an indicator of aggravated skin roughening, the distance will differ depending on the measuring conditions, and measurement is therefore carried out under a consistent condition. For example, if the thickness of the lipid membrane formed on the substrate is too small there will be greater variation in the distance, and if the thickness is too large it will be difficult to distinguish the border between the two. From the viewpoint of ensuring reproducibility, therefore, the lipid membrane has a thickness of preferably 5-100 μm and in particular about 50 μm. In addition, the shortest distance between the myelin figure and the skin intercellular lipid substrate increases with greater time from exposure to the surfactant and with higher temperature. From the viewpoint of minimizing variation, it is preferable to measure the myelin figure 6 hours after exposure, at a temperature of approximately 25° C. However, the method of evaluating skin roughening according to the invention is not limited to these conditions. The surfactant that is added can form a myelin figure in an essentially constant range if it is at or above the critical micelle concentration. Thus, when the surfactant is added at a constant concentration of at least the critical micelle concentration, the shortest distance between the tip of the myelin figure and the edge of the substrate will not vary significantly, and therefore the method of evaluating skin roughening according to the invention can be conducted in a high-concentration system, and with high reproducibility.

Concrete examples will now be provided for a more detailed explanation of the invention. However, the invention is not intended to be restricted by these examples.

Example 1

Preparation of Substrate Mimicking Intercellular Lipid in Stratum Corneum

Ceramide III (95.9%, 0.3 g) (product of Evonik Degussa, Essen, Germany), palmitic acid (0.15 g) (product of Nacalai Tesque, Inc., Kyoto, Japan) and cholesterol (0.15 g) (product of Nacalai Tesque, Inc., Kyoto, Japan) were dissolved in a mixed solvent of chloroform (50 $cm^3$) and methanol (10 $cm^3$). Next, the lipid mixture solution (0.2 $cm^3$) was spread onto 18×18 mm cover glass and dried. The produced lipid mixture membrane was melted in a glass tube oven at 120° C. and then allowed to stand for 1 hour in a nitrogen atmosphere at the same temperature. After cooling the sample to room temperature, it was permeated with water for 24 hours. Finally, it was stored in a desiccator (relative humidity: 75%) containing saturated sodium chloride until use.

Method of Evaluating Physical Properties of Stratum Corneum Intercellular Lipid Pseudosubstrate The stratum corneum intercellular lipid pseudosubstrate formed on cover glass was directly observed using an ECLIPSE TE 2000U microscope, (Nikon, Japan), and imaged using a pickup camera by Canon, Inc. Images were taken continuously once every minute. The differential scanning calorimetry (DSC) measurement was conducted using a DSC-100 (product of Seiko Instruments Inc., Japan) equipped with an SII SSC/5200 analyzer. X-ray diffraction (XRD) measurement was conducted with an X-ray diffraction apparatus (RAD-RC by Rigaku Co., Ltd., Japan and D8 Discover by Bruker, Germany) using high density CuKα radiation (λ=0.154 nm) monochromatized with a graphite monochromator, under conditions of 50 mA, 60 kV and 40 mA, 40 kV. The infrared (IR) absorption spectrum was obtained by measurement in transparent mode using KBr pellets, in a Digilab FTS-60A spectrometer by Bio-Rad. The spectra were all obtained with an average of 64 scans between 4000-400 $cm^{-1}$. The Raman spectrum was measured using a Bomem FT-Raman accessory (Bomem Inc., Canada), on an MB FT-IR optical bench mounting a germanium diode detector cooled with liquid nitrogen, with a Nd:Yag laser as the light source emitting near infrared rays of 533 nm.

DSC Measurement

Figure 2:
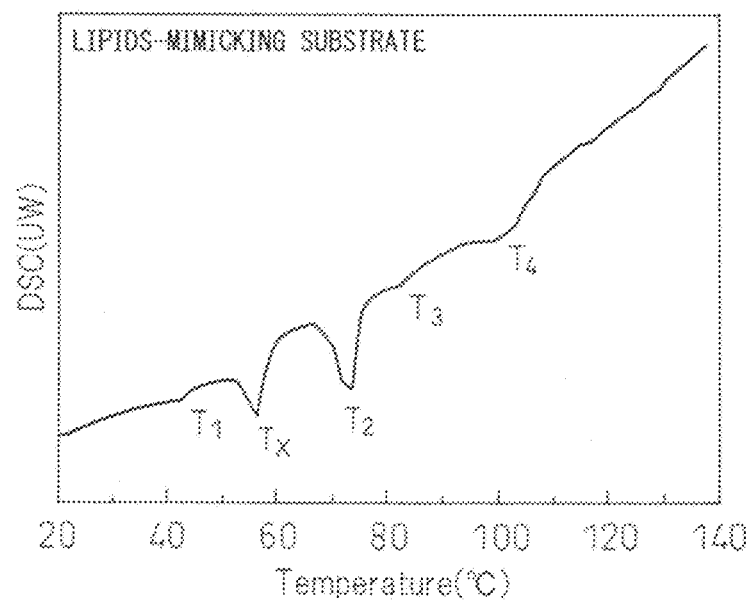
FIG. 2 is a DSC curve obtained by DSC of a substrate of the invention.

The substrate of the invention was subjected to DSC measurement, and 5 endothermic peaks: $T_1$ (42° C.), Tx (54.8° C.), $T_2$ (70° C.), $T_3$ (88° C.) and $T_4$ (100.2° C.), were confirmed (FIG. 2). The peak temperatures approximately matched the values for the human stratum corneum, according to the following table (Spectrochimica Acta Part A 1998, 54, 543-558.).

TABLE 1

| | Phase transition temperature (° C.) | | | | |
|---|---|---|---|---|---|
| | $T_1$ | $T_x$ | $T_2$ | $T_3$ | $T_4$ |
| Lipids-mimicking substrate | 42 | 54.8 | 70 | 88 | 100.2 |
| Human stratum corneum | 41-42 | 51-55 | 72 | 83 | 100 |

Since the phase transition temperature of the substrate differs from the melting point of each lipid alone, it is seen that the lipids composing the substrate of the invention do not exist as the simple lipid crystals but rather in a mixed state. The mixed state is highly similar to the human stratum corneum.

XRD Measurement

Stratum corneum intercellular lipids from the body comprise ceramides, fatty acids, cholesterol and the like as constituent components, and a lamellar structure is formed by blending these components. Two lamellar periodicities of stratum corneum intercellular lipids exist in mammals, 13 nm (long-periodicity lamellar structure) and 6 nm (short-periodicity lamellar structure).

A substrate of the invention composed of ceramide III, palmitic acid and cholesterol, prepared as described above, was subjected to X-ray diffraction (XRD) to examine the lamellar structure of the substrate. As a result, the majority of the lipids-mimicking substrate was found to have a lamellar spacing of 4.43 nm. This value differs from the value of the lamellar spacing formed by the lipids alone. Furthermore, the fact that the lamellar spacing was of a single type suggested miscibility of the lipids.

The results mentioned above demonstrated that a lamellar structure having a periodicity of 4.43 nm had been formed in the substrate of the invention. This periodicity differs from the lamellar periodicity in a lipid membrane from the body, but the difference exists only because only 3 different types of constituent lipids were used in the substrate of the invention. Despite the difference in periodicity, from the viewpoint of lipid miscibility and lamellar structure, the substrate of the invention can be concluded to be similar to the in vivo intercellular lipid structure of the stratum corneum.

Exposure of Substrate Mimicking Intercellular Lipids in Stratum Corneum to SDS Aqueous Solution Multiple substrates mimicking intercellular lipids in stratum corneum, each having a lipid membrane controlled to a thickness of 50 μm were exposed to an aqueous solution (5.0 mg/$cm^3$) of SDS (99.0%) (Nacalai Tesque, Inc., Kyoto, Japan) at a temperature of 25° C. for 6 hours. Each exposed substrate was rinsed with a small amount of water and dried, and used for the following evaluation test.

Microscopy

Figure 3:
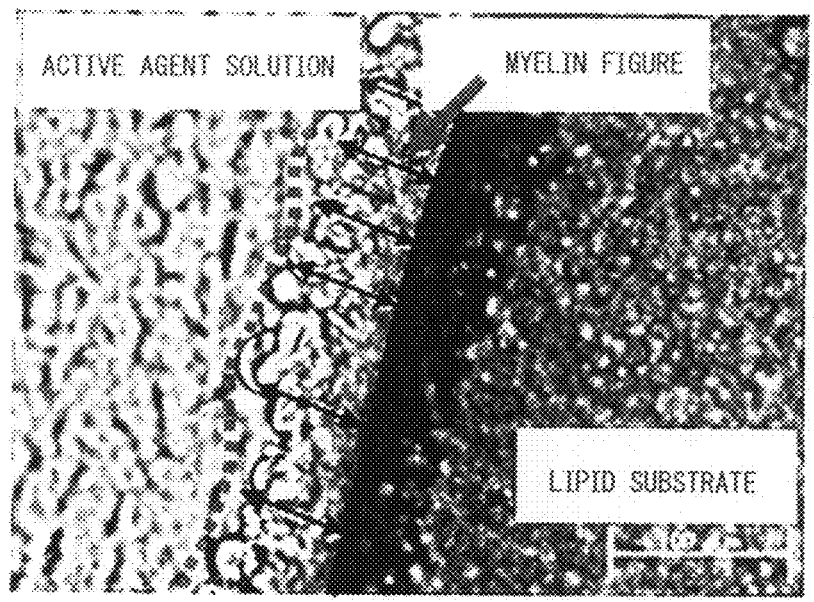
FIG. 3 is a microgram of a substrate after exposure to an aqueous SDS solution. A myelin figure was formed in a fixed range from the substrate.

Microscopy of the exposed substrate confirmed formation of a myelin figure within a constant range from the lipids-mimicking substrate (FIG. 3). Upon examination of surfactants other than SDS, a myelin figure was formed with some and not formed with others. For each of the examined surfactants, the shortest distance from the edge of the substrate to the tip of the myelin figure (hereunder referred to as "myelin figure formation distance") was measured. The results are shown in FIGS. 4 to 6.

Figure 4B:
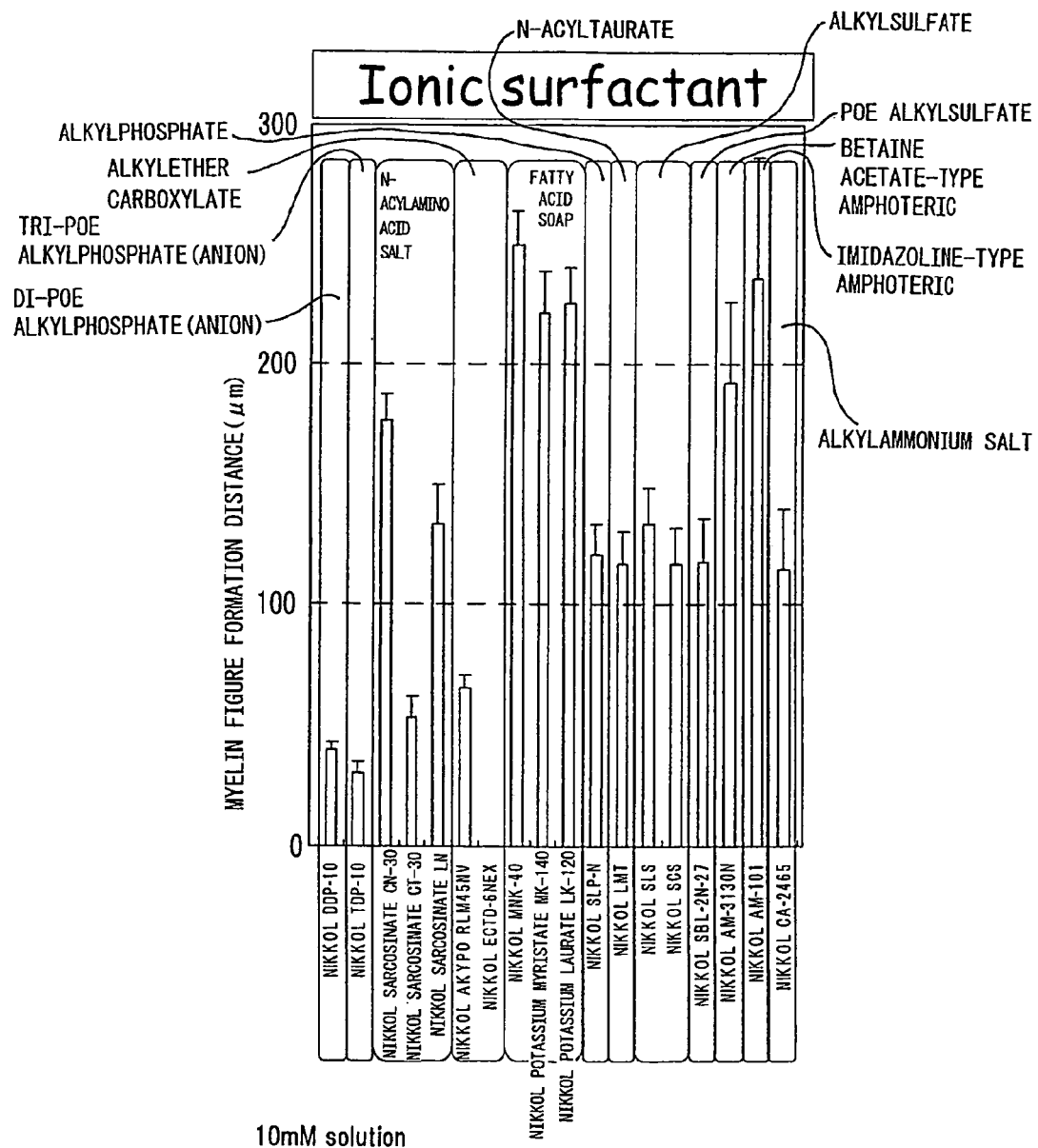
FIG. 4B is a graph showing the relationship between the ionic surfactants and the distances at which the myelin figures were formed.
Figure 6:
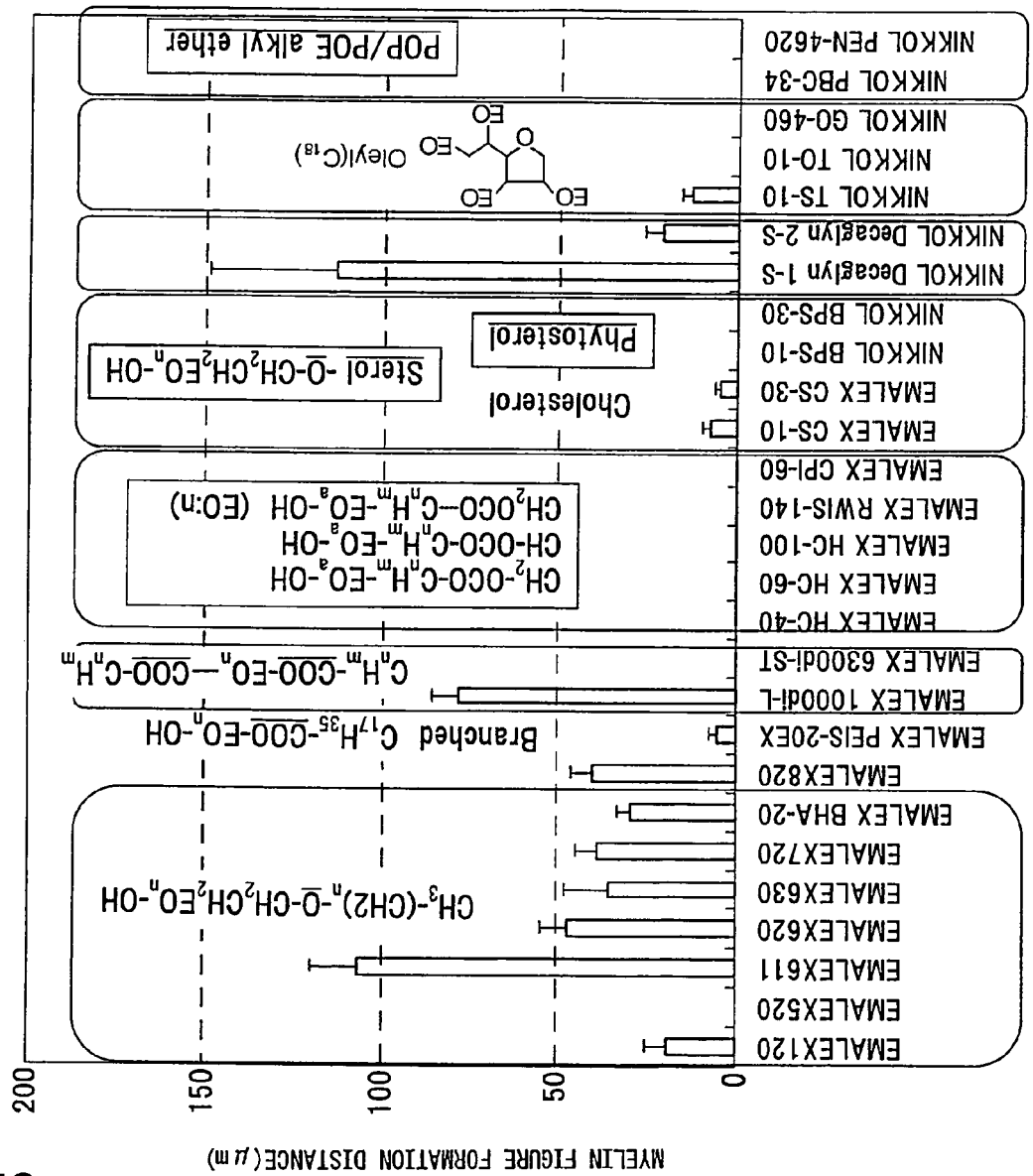
FIG. 6 is a graph showing the relationship between the nonionic surfactant structure and the distances at which the myelin figures were formed.

The results in FIGS. 4 to 6 show that a larger surfactant structure resulted in a greater myelin figure creation distance, and that ionic surfactants resulted in longer myelin figure formation distances than nonionic surfactants (see FIGS. 4A and 4B). Among the ionic surfactants, in particular, the myelin figure formation distance was longest with fatty acid soaps, followed by amphoteric surfactants and anionic surfactants. Nonionic surfactants had effects on the myelin figure formation distance, in the order of compounds with straight-chain alkyl ethers and cholesterol skeletons. Nonionic surfactants with branched alkyl ethers, glycerin skeletons and hydrogenated castor oil skeletons resulted in short myelin figure formation distances.

FIGS. 7 and 8 show the effects of alkyl chain length and mole number of added EO on myelin figure formation distance. The graphs show that longer alkyl chain length, and lower mole number of added EO, increase the myelin figure formation distance. A correlation was also found between surfactant molecular weight and myelin figure formation distance. As shown in FIG. 9, a smaller molecular weight was associated with longer myelin figure formation distance.

Correlation Between Myelin Figure Formation Distance and TEWL Value

Human arm skin was coated with a surfactant at 5% concentration (n=6, where one arm is n=1). The ΔTEWL value (g/$m^2$·h) was calculated based on the transepidermal water loss 1 hour after coating and the value immediately before coating. The results are shown in FIG. 10.

As seen by the results in FIG. 10, a high correlation was observed between the myelin figure formation distance and the ΔTEWL value. Since effusion of stratum corneum intercellular lipids by the surfactant is believed to be connected with myelin figure formation, this indicates that the correlation with the ΔTEWL value, as an evaluation index of in vivo skin roughening, is useful for evaluation of skin roughening using a substrate of the invention, which serves as an indicator of myelin figure formation.

INDUSTRIAL APPLICABILITY

The lipids-mimicking substrate of the invention can be utilized as an in vitro model substrate of stratum corneum intercellular lipids. The substrate of the invention has high structural homogeneity and facilitates measurement of changes in lipid structure. The substrate of the invention allows in vitro evaluation of skin roughening without using biological samples.

The invention claimed is:

1. An in vitro method for evaluating a potency of a surfactant for inducing skin roughening, comprising:
   adding a surfactant to an engineered substrate model mimicking intercellular lipids in stratum corneum, the engineered substrate model consisting of a non-biological substrate, and a lipid membrane formed on the substrate so as to have a lamellar structure, the lipid membrane comprising ceramides, palmitic acid, and cholesterol;
   visualizing for a myelin figure on the engineered substrate by microscope, and;
   judging:
   the surfactant as causing skin roughening in vivo when the myelin figure is formed on the engineered substrate, and
   wherein the surfactant is more potent for inducing skin roughening when the shortest distance between the tip of the myelin figure and an edge of the engineered substrate is longer.

2. The method of claim 1, wherein the ceramide, the palmitic acid, and the cholesterol are present in a mass ratio of 20-70%:10-60%:20-40% (ceramide:palmitic acid:cholesterol).

3. The method of claim 1, wherein the non-biological substrate is selected from the group consisting of a cover glass, mica, silicon wafer, stainless steel, and ceramic.

4. The method of claim 1, further comprising forming the lipid membrane on the substrate by:
   dissolving the ceramide, the palmitic acid, and the cholesterol in a mass ratio of 20-70%:10-60%:20-40% (ceramide:palmitic acid:cholesterol) in a solvent to form a solution;
   developing and drying the solution on the substrate to form the membrane;
   melting the membrane at a temperature higher than room temperature and cooling the membrane to the room temperature; and
   permeating the membrane with water.

5. The method of claim 1, further comprising forming the lipid membrane on the substrate by:
   melting a mixture of the ceramide, the palmitic acid, and the cholesterol in a mass ratio of 20-70%:10-60%:20-40% (ceramide:palmitic acid:cholesterol) at a temperature higher than room temperature;
   developing the molten mixture on the substrate to form the membrane and cooling the membrane to the room temperature; and
   permeating the membrane with water.

* * * * *